US011823790B2

(12) United States Patent
Adegboye et al.

(10) Patent No.: US 11,823,790 B2
(45) Date of Patent: Nov. 21, 2023

(54) AI DRIVEN ANESTHETIC PLANNING, MANAGEMENT AND CASE SCHEDULING TOOL FOR ANESTHESIOLOGISTS, RESIDENT PHYSICIANS, SURGEONS, PROCEDURALISTS, MID-LEVEL PROVIDERS AND OPERATING ROOM MANAGERS (AISCHPLAN)

(71) Applicants: Oluwajoba Adegboye, Chicago, IL (US); Ikechukwu Okafo, Niles, IL (US); Cletus Ajibade, St. Louis, MO (US)

(72) Inventors: Oluwajoba Adegboye, Chicago, IL (US); Ikechukwu Okafo, Niles, IL (US); Cletus Ajibade, St. Louis, MO (US)

( * ) Notice: Subject to any disclaimer, the term of this patent is extended or adjusted under 35 U.S.C. 154(b) by 346 days.

(21) Appl. No.: 17/241,426

(22) Filed: Apr. 27, 2021

(65) Prior Publication Data

US 2021/0335485 A1    Oct. 28, 2021

Related U.S. Application Data

(60) Provisional application No. 63/016,210, filed on Apr. 27, 2020.

(51) Int. Cl.
*G16H 40/20* (2018.01)
*G16H 20/40* (2018.01)
*G16H 10/60* (2018.01)

(52) U.S. Cl.
CPC ............ *G16H 40/20* (2018.01); *G16H 10/60* (2018.01); *G16H 20/40* (2018.01)

(58) Field of Classification Search
CPC ........ G16H 40/20; G16H 40/67; G16H 20/10; G16H 20/40; G16H 10/60; G16H 50/70; G16H 50/20; G16H 80/00
See application file for complete search history.

(56) References Cited

U.S. PATENT DOCUMENTS

| 5,006,050 | A  | * | 4/1991 | Cooke ...................... F04B 43/04 |
| | | | | 417/478 |
| 9,037,469 | B2 | * | 5/2015 | Opaluch .................. G10L 17/22 |
| | | | | 704/235 |
| 10,983,945 | B2 | * | 4/2021 | Molettiere ............. G16H 10/60 |
| 2008/0033894 | A1 | * | 2/2008 | Steck ...................... G16Z 99/00 |
| | | | | 706/12 |

(Continued)

*Primary Examiner* — Etienne P Leroux
(74) *Attorney, Agent, or Firm* — Jonathan B. David

(57) ABSTRACT

In an embodiment, a method includes accessing, by a processor configured within a device, a central system that provides trained data and crowd-sourced data to be used to schedule a plurality of medical services and treatment options. A module is configured to receive the trained data and crowd-sourced data from the central system, and pass the trained data and crowd-sourced data to an application, and provide predictive capabilities to the application based on the trained data and the crowd-sourced data. The processor uses the application to provide scheduling intervals for a series of medical services and treatments at one or more medical stations in real-time. Another device is connected to the first device, wherein the other device is configured to access the application and identify the scheduling intervals, and request updates and changes to the scheduling intervals in real-time.

20 Claims, 5 Drawing Sheets

(56) References Cited

U.S. PATENT DOCUMENTS

| | | | |
|---|---|---|---|
| 2008/0318192 A1* | 12/2008 | Jones | G09B 19/00 |
| | | | 434/247 |
| 2009/0240523 A1* | 9/2009 | Friedlander | G16H 20/10 |
| | | | 705/2 |
| 2016/0259908 A1* | 9/2016 | Hong | G06N 20/00 |
| 2017/0150446 A1* | 5/2017 | Kang | H04W 4/80 |
| 2019/0221317 A1* | 7/2019 | Kempanna | G10L 25/54 |
| 2020/0005912 A1* | 1/2020 | Saliman | G16H 10/60 |
| 2021/0008869 A1* | 1/2021 | Rodriguez Bravo | A61J 3/06 |

* cited by examiner

AI DRIVEN ANESTHETIC PLANNING, MANAGEMENT AND CASE SCHEDULING TOOL FOR ANESTHESIOLOGISTS, RESIDENT PHYSICIANS, SURGEONS, PROCEDURALISTS, MID-LEVEL PROVIDERS AND OPERATING ROOM MANAGERS (AISCHPLAN)

CROSS-REFERENCE TO RELATED APPLICATIONS

This application claims the benefit of U.S. Provisional Patent Application No. 63/016,210 filed on Apr. 27, 2020, being fully incorporated herein by reference.

BACKGROUND

Field of the Art

Embodiments of the present invention described herein generally relate to deploying artificial intelligence (AI) and machine-learning to provide predictive capabilities to an application or server to enable anesthetic planning and case scheduling for various surgical procedures.

Discussion of the State of the Art

Today, in several specialist hospitals within the United States of America and other countries, an average of three hundred and thirteen (313) million surgical cases and operations are carried out on an annual basis, at different times during the day. A key specialist that is highly indispensable before, during and after a surgical operation is the Physician Anesthesiologist (PA). Other personnel with different degrees of training who are involved in carrying out this activity under supervision of the PA include (Resident Physician Anesthesiologists, Certified Registered Nurse Anesthetists-CRNA and Anesthesiologist Assistant AA), assisted by Anesthesia Techs and the operating room nursing team. They meet with the patient before surgery to assess the patient's health (PRE-OP) and make decisions to ensure the anesthesia care or administration is as safe and effective as possible. They also monitor important vital signs and organ function during surgery, including how well the patient's heart and lungs and brain are functioning and administer appropriate medications or make necessary adjustments with ventilator settings or positioning or other interventions to ensure the patient is hemodynamically stable during the key phases of induction, maintenance and emergence (INTRA-OP). At the end of the surgery, the PA and allied staff also helps the patient recover and transition back to his/her complete consciousness (POST-OP). The PA also interacts with the Surgeon prior to, during and after the case to ensure that all surgical considerations that will affect the administration of the anesthetic and intraoperative anesthetic changes that will affect the surgery are discussed, clearly understood and agreed upon. The includes anesthetic procedures needed prior to surgery and the final disposition of the patient at the completion of the surgery.

A large teaching hospital may have as many as 100 PAs and allied staff with varying roles, assignments, skill and training level from day to day, who are assigned to several operation rooms (OR) with cases of varying complexity performed by diverse Surgeons across various hospital facilities and units. In addition to teaching hospitals, these surgical cases also take place in ambulatory surgery centers or outpatient settings where surgical procedures are also performed in private practice or teaching hospital settings (NORA—Non-OR-Anesthesia)

Creating the anesthetic plan for all phases of patient care and in some instances, managing the schedule and assigning the proper skilled staff to the appropriate case has been mostly accomplished manually. Such a system has many disadvantages and leaves the possibility for suboptimal, non-personalized anesthetic planning, and scheduling errors. As such, a system is needed that can overcome these real constraints that diminish PA effectiveness and place patients at higher risk.

A need exists to be able to have an efficient process of providing medical professionals, scheduled at set intervals with their patients, the ability to employ the most optimal and personalized anesthetic plan appropriately tuned to the surgical procedure. Further, a need also exists to have a streamlined approach to incorporate the patient's past medical and past surgical history in the development and fine tuning of the anesthetic plan and schedule with real time adjustments done intraoperatively. A need also exists to have additional recent medical history of the patients involved and incorporate into the anesthetic plan—including drug interactions, and status of the patient's key organ systems—neurologic, cardiovascular, pulmonary, hepatic, gastrointestinal, endocrine, hematologic and renal. Accordingly, a system is needed that eliminates a manual scheduling of treatments, and provides an efficient approach of scheduling medical professionals and appropriate treatments for patients in real-time using the past history of treatments and the medical history of the patients. Further, changes and updates to the schedules and treatment plans need to be updated efficiently in real-time when the need for changes and updates are required.

SUMMARY

The present invention overcomes the limitations described above by introducing an artificial intelligence and machine learning based method for providing predetermined and personalized anesthetic plans and schedules for medical professionals for anesthetic planning and treatments in hospitals/medical facilities.

In an embodiment, a method includes accessing, by a processor configured within a device, a central system that provides trained data and crowd-sourced data and machine learning derived data to be used to schedule a plurality of medical services and treatment options to one or more medical devices. The method also includes accessing, by the processor configured within the device, a module that is configured to receive the trained data and the crowd-sourced data from the central system, and pass the trained data and crowd-sourced data to an application, that provide predictive capabilities to the application based on the trained data and the crowd-sourced data. Further, the method includes accessing, by the processor configured within the device, the application that receives the predictive capabilities from the module including the trained data and crowd-sourced data, and using the application to provide scheduling intervals for a series of medical services and treatments at one or more medical stations in real-time. In addition, the method includes configuring another device to be connected to the first device, wherein the other device is configured to access the application and identify the scheduling intervals, and request updates and changes to the scheduling intervals in real-time.

In an embodiment, the application uses the crowd-sourced data to predict the treatment for one or more medical stations.

In an embodiment, the application uses the trained data to schedule the treatments at one or more medical stations.

In an embodiment, a method includes accessing, by a processor configured within a first device, a central system configured with the trained data and the crowd-sourced data, wherein the central system is connected to a module, wherein the central system is configured to transmit the trained data and the crowd-sourced data to the module. The method also includes accessing, by a second device connected to the first device, an application configured to receive the trained data and the crowd-sourced data from the module. The module provides the application with predictive capabilities; wherein the application enables medical services to be performed at set intervals based on the trained data and crowd-sourced data. The second device is configured to identify through the application, the set intervals with which the medical services are to be performed, and request changes and updates to the medical services through the application in real-time. The method also includes configuring a memory within at least one of the first device and the second device.

In an embodiment, the trained data and crowd-sourced data includes data on anesthetic planning and treatments.

In an embodiment, the trained data and crowd-sourced data includes data on past successful procedures.

In an embodiment, a system includes a processor configured within a first device, and configured to access a central system that provides trained data and crowd-sourced data to be used to schedule a plurality of medical services and treatment options to one or more medical stations. The system also includes a module configured to receive trained data and crowd-sourced data from the central system and pass the trained data and the crowd-sourced data to an application, and provide predictive capabilities to the application based on the trained data and the crowd-sourced data. The processor configured within the first device is configured to access the application that receives the trained data and crowd-sourced data from the module, and use the application to provide scheduling intervals for medical-related treatments at one or more medical stations. The system also includes a second device connected to the first device. The second device is configured to access the application to identify the scheduling intervals for the medical-related treatments at the one or more medical stations, and communicate with the first device to request changes and updates to the scheduling intervals. The system also includes a memory configured within the first or second device.

In an embodiment, the first device accesses the application to obtain records of past medical history.

In an embodiment, the trained data and the crowd-sourced data provide updates to anesthetic treatment plans in real-time.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

Figure 1:
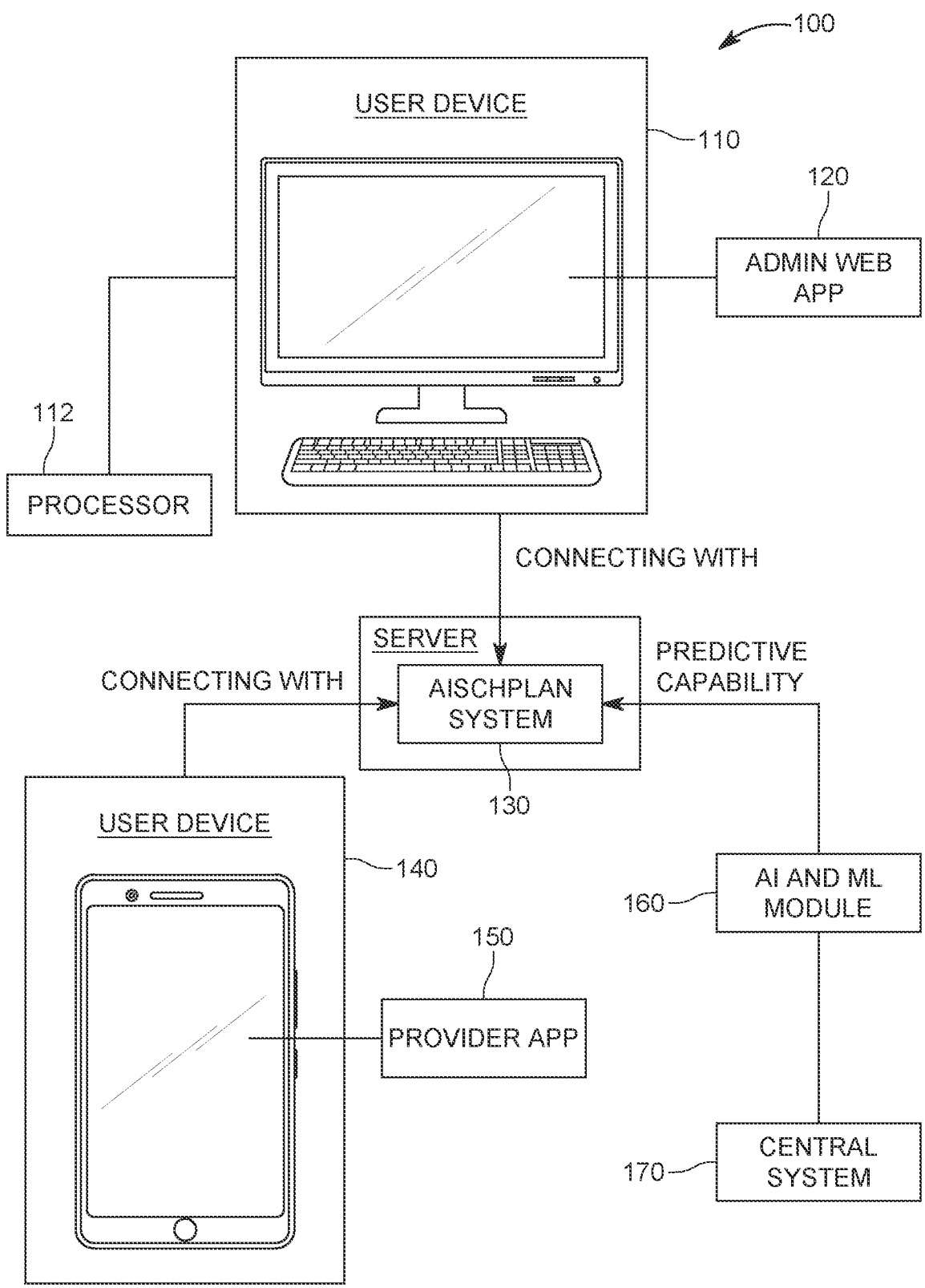
FIG. 1 illustrates an overview figure with respect to an embodiment of the present invention.

The present invention is for applying non-fixed personal perspective definitions with artificial intelligence machine learning in a computing device or computing system.

One or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

A system can be in place to successfully schedule medical professionals such as anesthesiologist and anesthesiologist assistants at one or more medical stations that treat patients. Moreover, an application or server known as Aischplan, can be configured to provide predictive treatments to patients and predictive scheduling for the medical professionals that administer the treatment to patients.

In an embodiment, a hospital administrator or the like can log onto a desktop computer or mobile device and access a central system. The central system can include crowd-sourced practitioner data, trained data derived from millions of previously administered, surgical case specific anesthetics and best practice data derived from decades of practice and safety improvements. The crowd-sourced practitioner data and trained data can include data on past treatments with regard to anesthetic planning and other related treatments. The crowd-sourced data and trained data can also include the pertinent medical history for each patient who will be receiving treatment. The central system can provide the crowd-sourced data and trained data, and thereby the predictive capabilities to an artificial intelligence and machine-learning module or AI and ML module. As such the user can also access the AI and ML module that receives the crowd-sourced data and trained data from the central system. The AI and ML module thereby receives the predictive capability from the central system.

The user can access the Aischplan system, which receives the crowd-sourced data and trained data from the AI and ML module. As such, the Aischplan receives the predictive capabilities from the AI and ML module. Accordingly, the administrator can use the Aischplan to schedule the anesthetic professionals/or medical professionals and the respective patients at various scheduling intervals. The crowd-sourced data and trained data can have the past history of the anesthetic planning and treatment, including which treatments were successful and which were not successful. The crowd-sourced data and trained data will also have the medical history of each current patient. As such, Aischplan can use the crowd-sourced data and trained data to efficiently schedule the medical professionals for scheduling intervals that will include the appropriate treatments and the respective patients as well.

The medical professional (such as an anesthesiologist or anesthesiologist assistant) can log onto his/her mobile device and be connected to the central server that drives the cloud based or locally hosted, HIPAA compliant application that drives the solution. The hospital administrator, staff anesthesiologist and operating room scheduling manager also have access to the application by logging via a desktop or mobile device. The medical professional can also access the Aischplan and identify his/her scheduling and timing intervals that include the assigned cases, AI driven anesthetic plan and patients. The medical professional can also communicate with the hospital administrator, and use the Aischplan to provide any updates or changes that are necessary based on the medical professionals expertise or due to changes in circumstances. The Aischplan can provide these changes in real-time, wherein the medical professional can communicate with the hospital administrator in real-time as well.

The Aischplan can be implemented and used by administrators and medical professionals within a hospital or medical facility to efficiently treat patients in a timely and efficient ways. The Aischplan provides a system of predictive capabilities using crowd-sourced data and trained data to predict when patients should be treated, and what the patients should be treated with as well.

In FIG. 1, a system 100 is illustrated. An administrator at a hospital or medical facility can log into a user device 110 (desktop or mobile device, etc.) to attempt to provide the updated schedules for doctors, nurses, and other health care professionals working at the hospital. The administrator can perform this task daily, and at various intervals within the same day. For instance, at the beginning of a day, the administrator can log onto the user device 110 to schedule the various medical professionals (doctors, nurses, etc.) for that particular day. Moreover, the administrator may also schedule each of the medical professionals for the entire week or the entire month.

In FIG. 1, the medical administrator can also note any potential changes that may occur during the scheduling period, and allow for potential changes to each schedule for the medical professionals. Such changes can be where one or more of the medical professionals or one or more of the patients having unforeseen circumstances that require a changing of the schedule or update in treatments. The administrator can access the administrator web application (admin web app) 120. In accessing the admin web app 120, the administrator can connect with the aischplan system (Aischplan) 130. The Aischplan can receive predictive capabilities from an AI and ML module 160. The AI and ML module 160 can receive the predictive capabilities from a central system 170.

In FIG. 1, the central system 170 can include the crowd-sourced data and trained data. The crowd-sourced data and trained data can include, but not limited to, the past history of treatment with regard to anesthetic planning. The crowd-sourced data and trained data can also include what treatments were successful and what treatments were not successful. In addition, the crowd-sourced data and trained data include the medical history for the patients involved. The central system 170 can pass the crowd-sourced data and sourced data to the AI and ML module 160. In turn, the AI and ML module 160 can pass the crowd-sourced data and trained data, and thereby the predictive capabilities to the Aischplan 130.

In FIG. 1, Aischplan 130 can be an application or server in one or more embodiments. In accessing the Aischplan 130, the administrator can determine how each medical professional should be scheduled for each day during a given scheduling period. Further, the administrator can account for various changes described above that may occur for each medical professional and/or patient during the scheduling period, and reschedule each of the medical professionals accordingly. The administrator may repeat the process of scheduling the medical professionals as necessary given the number of scheduling periods that the hospital may require.

Still referring to FIG. 1, a medical professional can log into a user device 140 to see his/her schedule for the day. The user device 140 can typically be mobile device such as a tablet or a cell phone. As mentioned above, the medical professional can be a doctor, nurse practitioner, or one with substantial similarities that may be working within the hospital or medical facility. The user can log in and see his/her schedule for the day. The user can log into a provider application (provider app) 150. Further, thru the provider app 150, the medical professional can access Aischplan 130 and see the times that he/she is scheduled, the cases, and also the type of cases that he/she is assigned. The predictive capabilities of Aischplan 130 can provide the scheduling intervals for the medical professional in real-time. Aischplan 130 also has the past medical history for each patient which the medical professional is treating, and the medical professionals can see the past medical history in real-time. As a result of seeing the schedule, the medical professional can make preparations for the cases that he/she is assigned. The medical professional can make the necessary mental preparations. The mental preparations can include how to relate to the patients involved with the particular case, and the level of attention that that particular patient for a particular case may require. Further, the medical professional can be prepared to work longer and/or shorter times based on the type of cases (in which length may vary) can require. The medical professional can also be aware of what type of treatments that he/she is likely to make given the predicted schedule. In addition, the medical professional can also be aware of any potential changes that may occur, such as different treatments that have to be given as a result of sudden and new developments and further follow up appointments with various patients. Further, the medical professional can also request updates and changes to the schedule due to unforeseen events using Aischplan 130. The medical professional can communicate with the administrator in real-time and access Aischplan 130, and have the scheduling and treatment be rescheduled and/or updated due to the unforeseen events or changes in circumstances.

In FIG. 1, Asischplan 130 has predictive capabilities for the scheduling and treatment planning. Aischplan 130 receives its predictive capabilities form an AL and ML module 160 illustrated which received the predictive capabilities from the central system 170. The crowd-sourced data and trained data can have the entire history of treatment the previous medical history for each patient. As such, Aischplan 130 can make predictions for each of the medical professionals in a given scheduling interval. Aischplan 130 can use data from the medical professionals recent treatment history and the patients' medical history to make the predictive treatments on the current cases that may be pending. As such, Aischplan 130 has the necessary predictive capabilities to enable for the scheduling of the medical professionals and treatments for various patients to function efficiently. In addition, as mentioned above, Aischplan 130 can allow the scheduling and treatments to be adjusted in response to changed and unforeseen circumstances in real-time.

Figure 2:
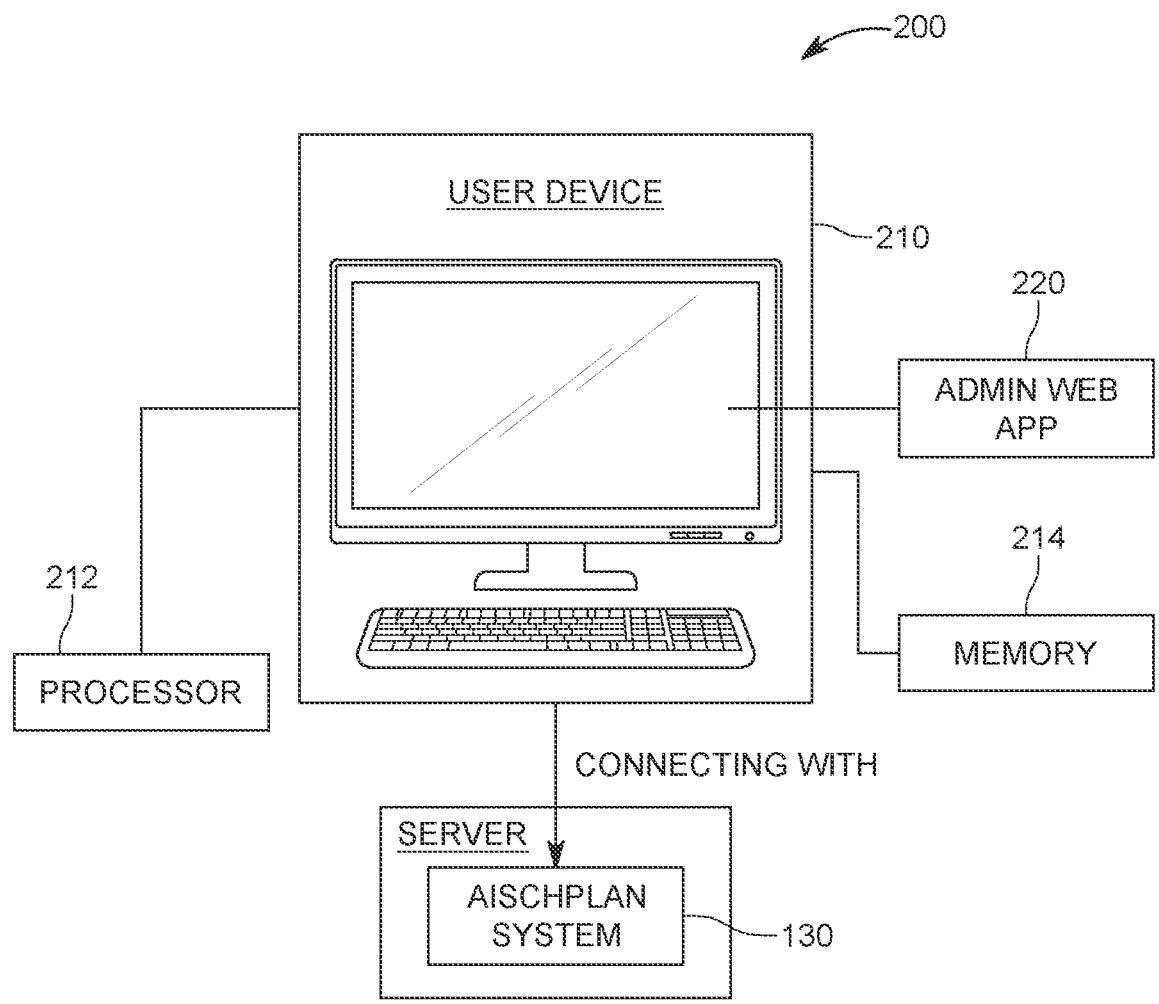
FIG. 2 illustrates a block diagram of an aspect of the present invention.

Referring to FIG. 2, a system 200 in which an administrator logs into a user device 210 to schedule the medical professionals for a scheduling interval. The administrator can be using a tablet or desktop computer. The scheduling interval can be anywhere for one day, one week, one month, or one quarter in one or more embodiments. The user device 210 can be configured with a processor 212 and memory 214.

In FIG. 2, the administrator logs into an administrator web application (administrator web app) 220 to schedule the medical professionals (doctors, nurses, etc.). The administrator also connects with an aischplan system (Aischplan) 130, which can be an application or server in a given embodiment. Through Aischplan 130, the administrator can efficiently schedule all of the medical professionals scheduled to work in the hospital/medical facility during the scheduling interval. Aischplan 130 can be configured with predictive capabilities due to crowd-sourced data and trained data it has received from an AI and ML module described in FIG. 1. The administrator can align the medical professionals with the appropriate patients. Further, Aischplan 130 may determine the length of each treatment interval based on the need and availability of patients based on the crowd-sourced data and trained data. Aischplan 130 can note the recent past scheduling of the medical professionals to determine any likely changes in the schedule that may need to occur. The Aischplan 130 will have the predictive capabilities to enable the administrator to schedule the medical professionals to provide the specific treatments during the scheduling interval.

In FIG. 2, Aischplan 130 can assist the administrator if changed or unforeseen circumstances require changes in scheduling and treatment. Moreover, In events of sudden occurrences that may occur during the middle of a scheduling interval, such as in the middle of a day, the administrator can also log into the administrator web app 220, and connect to Aischplan 130 to coordinate with any rescheduling of the medical professionals. The administrator can effectively access Aischplan 130 to ensure the time that each of the medical professionals use to help treat and attend to patients is used efficiently without the chaos of manually scheduling them at random intervals. The administrator, via Aischplan 130, can oversee initial scheduling and readjusted schedules to ensure maximum efficiency and treatment within the hospital/medical facility. As a result, the medical professionals will not have to spend any unnecessary time having to manually determine an order to their schedule.

Figure 3:
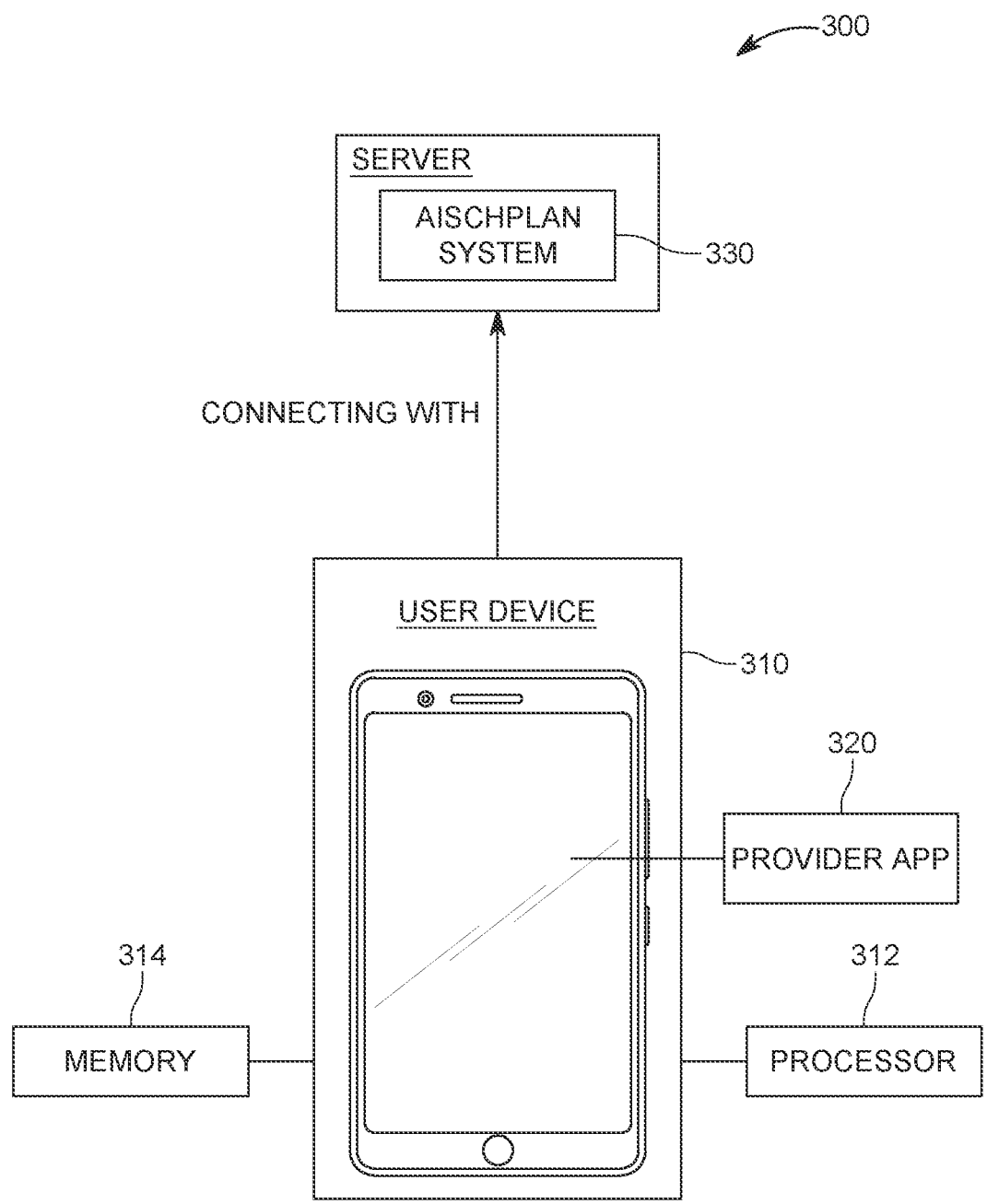
FIG. 3 illustrates another block diagram of an aspect of the present invention.

In FIG. 3, a system 300 is illustrated in which a medical professional such as an anesthesiologist, doctor, or nurse etc. logs into a user device 310 to see his/her schedule for a given scheduling period. The user device 310 can typically be a mobile phone or tablet. The medical professional can view a provider application (provider app) 320 via the user device 310.

In FIG. 3, at the beginning of a work day, the medical professional can log into the user device 310 and view the provider app. Further, the medical professional can connect with an aischplan system (Aischplan) 330 to view his/her schedule for a day or a week, and see the patients that are to be treated, and the length of each interval they may be scheduled to spend at various treatment stations within the hospital/medical facility. Aischplan 330 can be either an application or server in or more embodiments. The medical professional can also prepare additional treatments and medications and case preparations in response to viewing the schedule for the day. The medical professional being able to connect with the Aischplan 330 can enable the medical professional to prepare for each treatment schedule that he/she may be assigned. The medical professional may also be able to add further prescriptions or planning that may be necessary pursuant to his/her medical opinion based on the schedule. Further, by viewing the Aischplan 330, the medical professional will gain access to the trained data and the crowd-sourced data.

Referring to FIG. 3, the trained data and the crowd-sourced data contain all data on past treatments and scheduling. The past treatments and scheduling, can include, but are not limited to, past anesthetic planning and procedures that were successful and also were unsuccessful. The trained data and the crowd-sourced data can also include, but is not limited to, the medical history of each patient that has been treated and is going to be treated within the scheduling intervals. As such, the medical professional can use the trained data and the crowd-sourced data to prepare and plan for the scheduled treatments during the scheduling intervals.

In FIG. 3, in an embodiment, if unexpected events occur, the medical professional can connect with Aischplan 330 and also the administrator, who administers the schedule, to be able to rearrange the schedule based on the unexpected events that may require additional treatments and more medications at one particular treatment station. Moreover, the trained data and the-sourced data can enable for updated treatments and scheduling in real-time due to the unforeseen events. The crowd-sourced data and the trained data will have the entire past history for each patient and will enable the medical professional to be able to provide updated treatments and an updated schedule should a change in circumstance warrant an updated treatment and scheduling for a patient. Moreover, the medical professional can connect with Aischplan 330 and the medical administrator in real-time to discuss rescheduling due to unexpected events such sudden sicknesses of a patient or other medical emergencies that cannot have been foreseen. Accordingly, in addition to seeing his/her prearranged schedule, the medical professional is able to make changes via Aischplan 330 with the help of the predictive capabilities of Aischplan 330 in relation to the crowd-sourced data and trained data mentioned above.

The lack of structure or inefficient time management that may be present in other systems is not present because the medical professionals, due to seeing their scheduling efficiently arranged, know exactly what must be done at each treatment station throughout the work day. As the medical professionals know their schedule, their time along with their productivity can be maximized by the predictability of the schedule, and know what must be done and for how much time at each treatment station and/or treatment interval.

Figure 4:
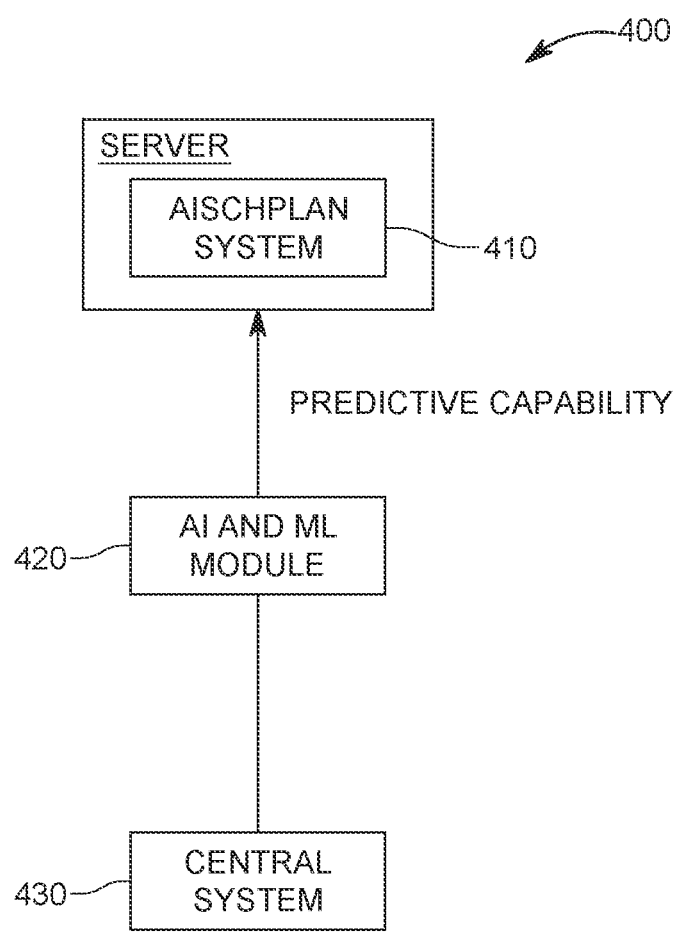
FIG. 4 illustrates a block diagram with respect to an embodiment of the invention.

In FIG. 4, a system 400 in which the predictive capability of the Aischplan system (Aischplan) 410 is illustrated. Aischplan 410 can provide predictive capabilities based on known data that has recently occurred. Schedules of the medical professionals in recent scheduling intervals can be used to predict future scheduling and treatment for the medical professionals. Aischplan 410 can be a server and/or application in or more embodiments.

In FIG. 4, a central system 430 can be configured with crowd-sourced data and trained data, which enable for predictive capabilities to be provided. The crowd-sourced data and trained data can have data that includes, but is not limited to, the entire past history of anesthetic planning and treatments. In addition, the crowd-sourced data and trained data can include, but is not limited to, having the past medical history of each patient that is to be treated during the scheduling intervals. As such, the crowd-sourced data and trained data provide the predictive capabilities for what treatment should be provided due to the data of past anesthetic planning and treatment and the medical history of each patient.

In FIG. 4, the AI and ML module 420 can provide Aischplan 410 with the predictive capability. The AI and ML module 420 can receive the crowd-sourced data and trained data from the central system 430. Further, the AI and ML module 420 can pass the predictive capabilities due to the trained data and the crowd-sourced data onto the Aischplan 410. The AI and ML module 420 can provide recent past data of the schedules and treatments that the medical professionals have provided due to the crowd-sourced data and the trained data. Moreover, the AI and ML module 420 can also provide the data in real-time to Aischplan 410 to help Aischplan 410 obtain further predictive capabilities, which can enable Aischplan 410 to determine the schedule, treatment, and case preparation in advance. Based on Aischplan 410 acquiring the predictive capabilities from the AI and ML module 420, Aischplan 410 can help the web administrator to administer the schedules for the medical professionals. Further, the medical professions (such as doctors, nurses), can see their daily schedules in real-time, and prepare accordingly, and/or request changes to their schedules due to their medical insight or some unexpected occurrences.

With respect to FIG. 4, the central system 430 and the AI and ML module 420 provides the critical and necessary predictive capabilities to Aischplan 410. Further, due to the crowd-sourced data and trained data, the AI and ML module 420 may identify past data that was used to schedule, treat and plan, and continuously provide the data needed to Aischplan 410 to have the predictive capability and each patient's medical history.

Figure 5:
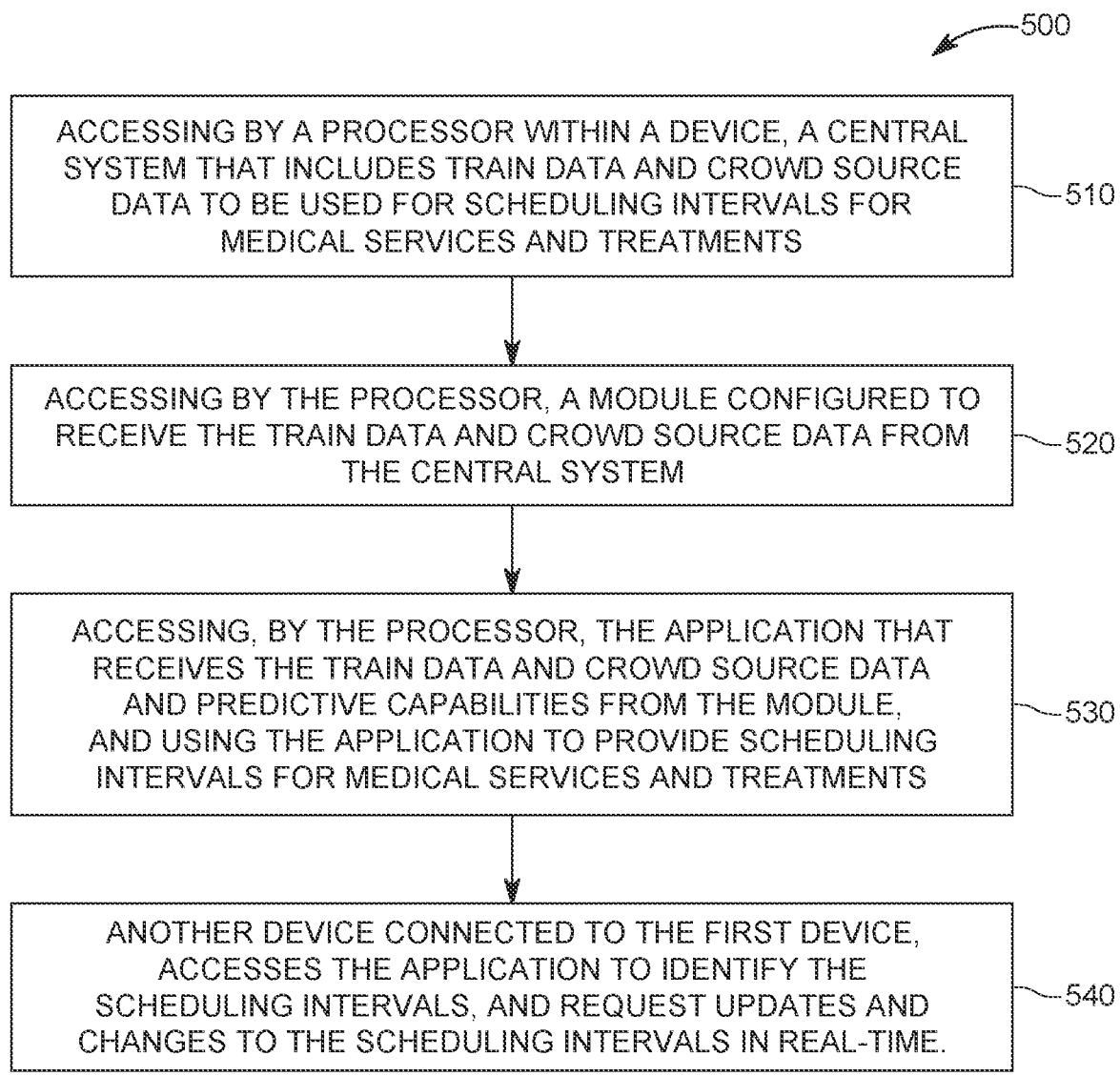
FIG. 5 illustrates a flowchart of an embodiment of the invention.

FIG. 5 illustrates a process 500 in which medical professionals such as anesthesiologists and anesthesiologist assistants or the like are able to see their treatments and schedules based on an Aischplan that provides predictive capabilities. Aischplan can receive the predictive capabilities from an AI and ML module, which received the predictive capabilities from a central system. Crowd-sourced data and trained data can make up the predictive capabilities. The trained data and crowd-sourced data can include, but not limited to, past treatments and schedules in regard to anesthetic planning and treatment, which can include both successful and unsuccessful procedures. The trained data and the crowd-sourced data can also include the medical history for each patient.

In FIG. 5, at step 510, a processor within a user device (desktop, mobile device) can access the central system. The central system can include the trained data and the crowd-sourced data that provides predictive capabilities. The trained data and crowd-sourced data have a history of past procedures and also the past medical history for each patient. The trained data and crowd-sourced data can be used for scheduling intervals for the medical services (anesthetic plans and treatments, etc.) and treatments.

In FIG. 5, at step 520, the processor within the user device can also access the AI and ML module. The AI and ML module can be connected to the central system. As such, the AI and ML module can receive the trained data and crowd-sourced data from the central system. As such, the AI and ML module will receive the predictive capabilities with crowd-sourced data and trained data, wherein the past history of treatments and past medical history of patients is known and used for future predictive scheduling and treatments.

In FIG. 5, at step 530, the processor within the user device can access the application/server Aischplan. Aischplan receives the trained data and the crowd-sourced data from the AI and ML module. Aischplan can provide the predictive capabilities needed to schedule the anesthetic treatments for the medical professionals. The crowd-sourced data and trained data can enable the predictive capabilities to be provided for the Aischplan. Moreover, Aischplan can provide updates in real-time. As such, a user such as a hospital administrator can use the Aischplan to schedule the upcoming treatments for various patients.

In FIG. 5, at step 540, another device can be connected to the first device. An anesthesiologist, or medical professional can have a mobile device and be connected to the hospital administrator who is accessing the other user device. The medical professional, through his/her user device, can access Aischplan and identify the scheduling intervals and treatments that have been assigned. In addition, due to changes in circumstances, the medical professional can use Aischplan to request updates and changes to the scheduling intervals in real-time. The medical professional, using Aischplan, can contact the hospital administrator, and have updates to treatments and the schedules be provided. The predictive capabilities of Aischplan due to the crowd-sourced data and trained data allow updates to treatments and schedules to be provided in real-time.

Accordingly, the Aischplan system can streamline the process with which medical professionals involved in anesthetic planning and treatment spend each day attending to and treating patients. The use of manual scheduling can be eliminated. The crowd-sourced data and trained data provide predictive capabilities. Updates to treatments and schedules can be provided in real-time. The crowd-sourced data and trained data will have updated information on all the treatments that have been performed (with respect to anesthetic planning and treatments, etc.) and also have the pertinent medical history for each patient. In addition, should unforeseen circumstances occur, the predictive capabilities of Aischplan help to provide updates and changes to scheduling and treatment in real-time. Medical professionals will not need to manually schedule treatments on a daily basis as a result. The Aischplan system can give predictability and certainty to the schedule of medical professionals, and also account for unexpected scheduling changes that may occur. The efficiency of anesthetic treatment and planning can therefore be greatly enhanced due to the Aischplan system.

Exemplary user devices are illustrated in some of the figures provided herein. This disclosure contemplates any suitable number of user devices, including computing systems taking any suitable physical form. As example and not by way of limitation, computing systems may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, or a combination of two or more of these. Where appropriate, the computing system may include one or more computer systems; be unitary or distributed; span multiple locations; span multiple machines; or reside in a cloud, which may include one or more cloud components in one or more networks. Where appropriate, one or more computing systems may perform without substantial spatial or temporal limitation one or more steps of one or more methods described or illustrated herein. As an example, and not by way of limitation, one or more computing systems may perform in real time or in batch mode one or more steps of one or more methods described or illustrated herein. One or more computing systems may perform at different times or at different locations one or more steps of one or more methods described or illustrated herein, where appropriate.

In particular embodiments, one or more data storages may be communicatively linked to one or more servers via one or more links. In particular embodiments, data storages may be used to store various types of information. In particular embodiments, the information stored in data storages may be organized according to specific data structures. In particular embodiments, each data storage may be a relational database. Particular embodiments may provide interfaces that enable servers or clients to manage, e.g., retrieve, modify, add, or delete, the information stored in data storage.

While exemplary embodiments are described herein, it is not intended that these embodiments describe all possible forms of the invention. Rather, the words used in the specification are words of description rather than limitation, and it is understood that various changes may be made without departing from the scope of the invention. Additionally, the features of various implementing embodiments may be combined to form further embodiments of the invention.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the embodiments disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific embodiments, at least some of the features or functionalities of the various embodiments disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some embodiments, at least some of the features or functionalities of the various embodiments disclosed herein may be implemented in one or more virtualized computing environments (e.g., network computing clouds, virtual machines hosted on one or more physical computing machines, or other appropriate virtual environments).

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

Because such information and program instructions may be employed to implement one or more systems or methods described herein, at least some network device embodiments may include non-transitory machine-readable storage media, which, for example, may be configured or designed to store program instructions, state information, and the like for performing various operations described herein. Examples of such non-transitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "SSD" storage drives that may combine physical components of solid state and hard disk drives in a single hardware device (as are becoming increasingly common in the art with regard to personal computers), storage memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

In various embodiments, functionality for implementing systems or methods of various embodiments may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various embodiments described above. Accordingly, the present invention is defined by the claims and their equivalents.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. A system, comprising:
accessing, by a processor configured within a device, a central system that provides trained data and crowd-sourced data to be used to schedule a plurality of medical services and treatment options to one or more medical stations;
accessing, by the processor configured within the device, a module that is configured to receive trained data and crowd-sourced data from the central system, and pass the trained data and crowd-sourced data to an application, and provide predictive capabilities to the application based on the trained data and the crowd sourced data;
accessing, by the processor configured within the device, the application that receives the predictive capabilities from the module including the trained data and the crowd-sourced data, and using the application to provide scheduling intervals for a series of medical services and treatments at one or more medical stations in real-time, wherein the application includes information on a level and type of treatment required to treat each patient; and configuring another device to be connected to the first device, wherein the other device is configured to access the application and identify the scheduling intervals, and request updates and changes to the scheduling intervals in real-time.

2. The method of claim 1, wherein the predicting of the treatments is made continuously in real-time.

3. The method of claim 1, wherein the scheduling of necessary treatments is seen in real-time.

4. The method of claim 1, wherein the predictive capabilities include determining the prediction of treatment from past medical history.

5. The method of claim 1, further comprising:
gathering anesthetic plans based on the treatment predicted for the one or more medical stations, wherein the data validation rules include self-referential rules.

6. The method of claim 1, wherein the application uses the crowd-source data to predict the treatments for one or more medical stations.

7. The method of claim 1, wherein the application uses the trained data to schedule the treatments at one or more medical stations.

8. A method comprising:
accessing, by a processor configured within a first device, a central system configured with trained data and crowd-sourced data, wherein the central system is connected to a module, wherein the central system is configured to transmit the trained data and crowd-sourced data to the module;
accessing, by a second device connected to the first device, an application configured to receive the trained data and the crowd-sourced data from the module, wherein the module provides the application with predictive capabilities, wherein the application enables medical services to be performed at set intervals based on the trained data and crowd-sourced data, and wherein the second device is configured to identify through the application the set intervals with which the medical services are to be performed, wherein the application includes information on a level and type of treatment required to treat each patient, and wherein the second device requests changes and updates to the medical services through the application in real-time; and
configuring a memory within at least one of the first device and the second device.

9. The method according to claim 8, wherein the trained data and crowd-sourced data includes data on anesthetic planning and treatments.

10. The method according to claim 8, wherein the trained data and crowd-sourced data includes data on past successful procedures.

11. The method according to claim 8, wherein the crowd-sourced data and trained data enables the first device and second device to receive updates in real-time.

12. The method according to claim 8, wherein the first device uses the application to make changes to the set intervals in real-time.

13. The method according to claim 8, wherein the second device notifies the first device of scheduling changes that need to be made.

14. The method according to claim 8, wherein the crowd-sourced data and the trained data enable the first device to access the application and make changes to the set intervals in real-time.

15. A system comprising:
a processor configured within a first device, and configured to access a central system that provides trained data and crowd-sourced data to be used to schedule a plurality of medical services and treatment options to one or more medical stations;
a module configured to receive the trained data and the crowd sourced data from the central system and pass the trained data and crowd-sourced data to an application, and provide predictive capabilities to the application based on the trained data and crowd-sourced data, wherein the processor configured within the first device is configured to access the application that receives the trained data and the crowd-sourced data from the module, and use the application to provide the scheduling intervals for medical-related treatments at one or more medical stations;
a second device connected to the first device, wherein the second device is configured to access the application to identify the scheduling intervals for the medical-related treatments at the one or more medical stations, and communicate with the first device to request changes and updates to the scheduling intervals, wherein the application includes information on a level and type of treatment required to treat each patient; and
a memory configured within the first or second device.

16. The system of claim 15, wherein the first device accesses the application to obtain records of past medical history.

17. The system of claim 15, wherein the trained data and crowd-sourced data provide updates to anesthetic treatment plans in real-time.

18. The system of claim 15, wherein unforeseen events are communicated by the second device to the first device to enable the changes and updates to be provided.

19. The system of claim 15, wherein the first device receives changes and updates from the application in real-time due to the crowd-sourced data and the trained data.

20. The system of claim 15, wherein the crowd-sourced data and trained data include data of past anesthetic planning treatments that will be used for the medical-related treatments in the scheduling intervals.

* * * * *